(12) United States Patent
Farage

(10) Patent No.: US 8,568,314 B2
(45) Date of Patent: Oct. 29, 2013

(54) METHOD FOR ASSESSING SUBSURFACE IRRITATION OF SKIN

(75) Inventor: Miranda Aref Farage, Mason, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 883 days.

(21) Appl. No.: 11/715,625

(22) Filed: Mar. 8, 2007

(65) Prior Publication Data

US 2008/0221405 A1    Sep. 11, 2008

(51) Int. Cl.
*A61B 5/00* (2006.01)
*F21V 9/02* (2006.01)

(52) U.S. Cl.
USPC ............................................ 600/306; 362/19

(58) Field of Classification Search
USPC ............... 600/306; 359/204.3, 207.9; 433/29; 362/19
See application file for complete search history.

(56) References Cited

U.S. PATENT DOCUMENTS

| | | | |
|---|---|---|---|
| 5,160,315 A | 11/1992 | Heinecke et al. | |
| 5,531,855 A | 7/1996 | Heinecke et al. | |
| 5,897,509 A * | 4/1999 | Toda et al. | 600/589 |
| 6,426,444 B2 | 7/2002 | Roe et al. | |
| 6,515,029 B1 | 2/2003 | Krzysik et al. | |
| 6,924,256 B2 * | 8/2005 | Massaro et al. | 510/119 |
| 2003/0069482 A1 | 4/2003 | Workman, Jr. et al. | |
| 2004/0003670 A1 | 1/2004 | Minerath, III et al. | |
| 2005/0030372 A1 * | 2/2005 | Jung et al. | 348/77 |
| 2005/0146863 A1 * | 7/2005 | Mullani | 362/140 |
| 2005/0154382 A1 * | 7/2005 | Altshuler et al. | 606/9 |
| 2007/0237374 A1 * | 10/2007 | Nikiforos et al. | 382/128 |
| 2008/0080766 A1 | 4/2008 | Payonk et al. | |

OTHER PUBLICATIONS

Farage et al. "Development of a sensitive test method to evaluate mechanical irritation potential on mucosal skin", Skin Researh and Technology 2004; 10: 85-95.*
Assessing the Skin Irritation Potential of Facial Tissues, Miranda A. Farage, Cutaneous and Ocular Toxicology, 24: 125-135, 2005.
Correlating Sensory Effects with Irritation, Miranda A. Farage, Marie-Vee Santana and Elizabeth Henley, Cutaneous and Ocular Toxicology, 24: 45-52, 2005.
Cutaneous and Sensory Effects of Two Sanitary Pads with Distinct Surface Materials: A Randomized Prospective Trial, Miranda Farage, Alexandra Katsarou and Eugenia Tsagroni, Philip Bowtell, Sandy Meyer, Aikaterini Deliveliotou and George Creatsas, Cutaneous and Ocular Toxicology, 24: 227-241, 2005.
Mauricio R. Odio, Robert J. O'Connor, Frank Sarbaugh, & Sue Baldwin, Procter & Gamble Co., Cincinnati, OH, Continuous Topical Administration of a Petrolatum Formulation by a Novel Disposable Diaper, Pharmacology and Treatment, Dermatology 2000; 200-238-243, © 2000 S. Karger AG, Basel.

(Continued)

*Primary Examiner* — Patricia Mallari
*Assistant Examiner* — Eric Messersmith
(74) *Attorney, Agent, or Firm* — Sarah M. DeCristofaro; James E. Oehlenschlager

(57) ABSTRACT

A method for determining skin irritation is provided. The method uses a source of cross-polarized light to illuminate and area of skin. The cross-polarized light is used to detect subsurface indicators of skin irritation such as erythema, inflammation, dryness, or innervation. The subsurface indicator is then assigned a score.

7 Claims, 3 Drawing Sheets

(56) References Cited

OTHER PUBLICATIONS

Miranda A. Farage, Debbie A. Gilpin, Ninah A. Enane & Sue Baldwin, Procter & Gamble Co., Winton Hill Tech Center, Sharon Woods Tech Center & Baby Care Products, Cincinnati, OH, Development of a new test for mechanical irritation: behind the knee as a test site, Skin Research and Technology 2001; 7:193-203, Printed, Denmark. © Munksgaard, 2001, Pub. Aug. 22, 2000.

Miranda A. Farage, Sandy Meyer & David Walter, Procter & Gamble Co., Winton Hill Tech Center, Cincinnati, OH, Development of a sensitive test method to evaluate mechanical irritation potential on mucosal skin, Skin Research and Technology 2004; 10:85-95, Printed, Denmark. © Blackwell Munksgaard, 2004, Pub. Sep. 8, 2003.

Miranda A. Farage, Sandy Meyer & David Walter, Procter & Gamble Co., Winton Hill Tech Center, Cincinnati, OH, Evaluation of modifications of the traditional patch test in assessing the chemical irritation potential of feminine hygiene products, Skin Research and Technology 2004; 10:73-84, Printed, Denmark. © Blackwell Munksgaard, 2003, Pub. Sep. 8, 2003.

S. Baldwin, M. R. Odio, S. L. Haines, R. O'Connor, S. Englehart, A. T. Lane, Procter & Gamble Co., Stanford University School of Medicine, Palo Alto, CA, Procter & Gamble Co., 11450 Grooms Road, Cincinnati, OH, Skin benefits from continuous topical administration of a zinc oxide/petrolatum formulation by a novel disposable diaper, JEADV (2001) 15(Suppl. 1)5-11, © 2001 European Academy of Dermatology and Venereology.

The Vulvar Epithelium Differs From the Skin: Implications for Cutaneous Testing to Address Topical Vulvar Exposures, Miranda Farage and Howard I. Maibach, Contact Dermatitis, 2004: 51: 201-209.

Vulvar Susceptibility to Contact Irritants and Allergens: A Review, Miranda, A Farge, Arch Gynecol Obstet (2005) 272; 167-172.

"Polarized light photography in the evaluation of photoaging" Joseph A. Muccini, MD et al., Journal of the American Academy of Dermatology, vol. 33, No. 5, Part 1, Nov. 1995, pp. 765-769.

"Correlating Sensory Effects With Irritation" Miranda A. Farage et al., Cutaneous and Ocular Toxicology, 24: 45-52, 2005, Taylor & Francis, Inc., pp. 45-52.

"Are we reaching the limits or our ability to detect skin effects with our current testing and measuring methods for consumer products?" Miranda A. Farage, Contact Dermatitus 2005: 52: Mar. 30, 2005, pp. 297-303.

"Polarized light photography enhances visualization of inflammatory lesions of acne vulgaris" Scott B. Phillips, MD et al., Journal of the American Academy of Dermatology, Dec. 1996, vol. 37, No. 6, pp. 948-952.

The article "Stemlaser Exploring Solutions," by Rox Anderson, MD, was the result of an internet search and had no publication date listed. As such Applicant is supplying the date the reference was found on the internet (date found Jan. 31, 2007). Location: http://www.sternlaser.co.za/ProdSyrisTech.asp, V600 and V300 Technical Basis pp. 1-2.

Primavera B., Carrera M., and Berardesca E., "Tests for Sensitive Skin," In: Paye M, Barel AO, Maibach HI, eds. Handbook of Cosmetic Science and Technology, $2_{nd}$ ed. Boca Raton: CRC Press, Taylor and Francis Group, 2006: 733-743.

* cited by examiner

Saline 0.025% SLS 0.05% SLS 0.1% SLS

Forearm, 2-hour patch

Forearm, 6-hour patch

Upper arm, 2-hour patch

Upper arm, 6-hour patch

METHOD FOR ASSESSING SUBSURFACE IRRITATION OF SKIN

FIELD OF THE INVENTION

The present invention relates to methods using cross-polarized light to assess skin irritation.

BACKGROUND OF THE INVENTION

Testing is done to assess a personal care article's safety. One avenue of testing personal care articles, such as diapers or feminine hygiene pads, involves contacting the article with human skin. Many different tests are used to assess skin irritation caused by such contact. Examples of tests include standard occluded patch tests, and tests that contact a chemical agent contained in personal care articles with skin. The skin contacted by the personal care article or chemical agent is then assessed to determine the presence of any irritation.

Due to safety concerns, most personal care articles that will cause a strong or immediate skin reaction (irritation) are not tested on human subjects. Rather, personal care articles that produce either minor irritation effects, or that produce irritation over prolonged exposure, are tested using human skin. To visually detect an irritation reaction before it causes undue discomfort to a test subject can be difficult, even for trained technicians.

Like other types of inflammation reactions, irritation of the skin triggers a series of events involving subsurface dilation of blood vessels, and an influx of inflammatory cells to the irritated area of skin. Irritated areas of skin often take on a red hue or coloration as compared to the un-irritated surrounding areas of skin. In addition, a change of color in the irritated skin may be accompanied by swelling and heat.

Most methods of testing for irritation caused by a personal care article rely on an objective visual evaluation of how the personal care article affects the outer surface of the skin. In contrast, the concerns of users are generally subjective in nature, and are a product of the evaluation of negative sensations caused by the personal care article, such as itchy, dry, rough, or tight skin. Often these sensations are caused by irritation that is not apparent on the outward appearance of the skin.

It would be desirable to provide a method that detects even minor levels of skin irritation in human test subjects. Further, it would be desirable to provide a method to detect skin irritation before it is noticeable on the outer surface of the skin.

SUMMARY OF THE INVENTION

A method of assessing skin irritation is provided. The method comprises the steps of providing a source of cross-polarized light, which is used to illuminate and area of skin. The illuminated area of skin is viewed using the cross-polarized light to detect a subsurface indicator of skin irritation. The subsurface indicator is then assigned a score.

Another method of assessing skin irritation is provided. The method comprises the steps of providing a personal care article and contacting the personal care article with an area of skin. A source of cross-polarized light is also provided. The source of cross-polarized light is used to illuminate an area of skin. The illuminated area of skin is viewed using the cross-polarized light to detect a subsurface indicator of skin irritation.

DETAILED DESCRIPTION OF THE INVENTION

Figure 1A:
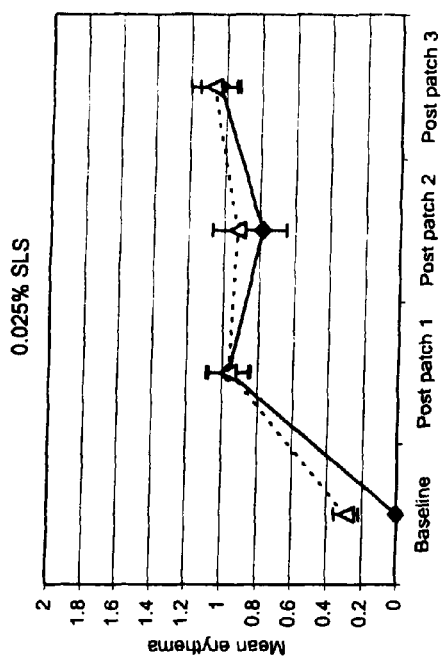
FIG. 1A is a graph illustrating the visual and subsurface mean erythema scores of upper arm test sites to which a patch containing saline has been applied.

As used herein, the term "personal care article" refers to a substrate or chemical agent that is applied to, or contacted with, a portion of the body such as the skin, hair, or teeth. For example personal care articles may be feminine care products (feminine hygiene pads, catamenial tampons, wipes), adult incontinence products, sanitary tissue products (facial tissue, toilet tissue, paper towels, wipes), baby care products (diapers, wipes), home care products (cleaning wipes, dusting wipes), beauty care products such as wipes, and oral care products (toothpaste, mouthwash).

The term "substrate" as used herein refers to woven material, non-woven material, or film material which is applied to, or contacted with, the body.

The term "irritation", or "irritate", or "irritating", as used herein, refers to an area of skin which exhibits indications of skin irritation such as erythema, inflammation, dryness, or innervation. In certain embodiments, irritation may be caused by chemical means or physical means.

The term "chemical means", as used herein, refers to a chemical agent which irritates an area of skin.

The term "physical means", as used herein, refers to a substrate that contacts an area of skin in such a manner as to cause irritation to the area of skin. Examples of physical means include tape stripping an area of skin, rubbing a substrate across an area of skin, and occluding an area of skin from the external environment.

The term "erythema", as used herein, refers to redness of the skin.

The term "dryness", as used herein, refers to powderiness or cracking of the skin.

The term "inflammation", as used herein, refers to a local response to cellular injury that is marked by capillary dilatation.

The term "innervation", as used herein, refers to the presence of neural tissue.

The present invention is a reliable method for assessing skin irritation. The method uses polarized light, and a polarized viewer to produce cross-polarized light to detect subsurface indicators of skin irritation such as erythema, inflammation, dryness, or innervation. These indicators of skin irritation are often detected in the skin subsurface of users of personal care articles who experience negative sensations such as, itchy, dry, rough, or tight skin during or after use of the personal care article.

When light encounters the skin surface, about five percent (5%) is reflected. This reflected light only carries information about the shape and texture of the skin surface. The remaining 95% of light enters the skin, where it encounters structures that either scatter or absorb the light. Some of the light that is scattered exits out of the skin. This back-scattered light component carries information about subsurface skin structures such as blood vessels, pigmentation, hair follicles, skin color, and inflammation. Back scattering scrambles polarization, which is the orientation of light waves, whereas light reflected from the skin surface does not. Therefore, an instrument such as the v600, produced by Syris Scientific LLC. of Gray, Me., that uses a polarized illuminating light, combined with polarized viewing, separates the two components (specular reflection/back scattering) of skin reflectance. By crossing the polarizing illuminating light and viewing polarizers to produce a source of cross-polarized light, the reflected component is blocked, providing a greatly enhanced view below the skin surface (subsurface).

While not critical to the invention, the selection of test participants is done according to practices and criteria well known in the art. For example, in one embodiment test participants are selected according to skin type as determined using Fitzpatrick's classifications, as disclosed in The Validity And Practicality Of Sun-Reactive Skin Types I Through VI. Archives Dermatology 1988 June; 124(6):869-71.

As one skilled in the art will recognize, the methods described herein can be applied to various areas of the skin, or other areas of the body where subsurface irritation can be detected using cross-polarized light, such as mucosal tissue in the mouth, or elsewhere. However, in certain embodiments, the area of the skin includes forearm skin, upper arm skin, and/or the skin at the back of the knee (popliteal fossa). It will be understood by one of ordinary skill in the art that areas of skin comprises both normal (healthy) skin, and skin which is abnormal or damaged, such as melanoma and burned skin.

In certain embodiments, irritation may be induced in an area of skin by chemical means or physical means. An example of the use of chemical means to irritate an area of skin may include contacting the area of skin with a skin irritant agent, for instance sodium lauryl sulfate and sodium laureth sulfate. An example of the use of physical means to irritate an area of skin may include tape stripping the area of skin. As known by one of skill in the art, tape stripping comprises applying a piece or pieces of tape to an area of skin, and then removing the tape such that the area of skin becomes irritated. Another example of physical means may include occluding an area of skin. One method of occluding comprises placing a patch, such as a Webril® patch, (Professional Medical Products Company) over an area of skin. Tape, such as an occlusive, hypoallergenic tape, such as Blenderm® tape, (3M Company) may be used to cover the patch and hold the patch in place on an area of skin. The patch may also comprise a chemical agent to facilitate irritation of the skin.

The methods of the present invention may be used to determine if the treatment of an area of skin with a lotion provides a benefit. For example, the methods of the present invention may include pretreatment (before being assessed using cross-polarized light) or post-treatment (after being assessed using cross-polarized light) of an area of skin with a lotion. This would help determine whether a lotion affects irritation on an area of skin. For example, an area of skin may be irritated, but before the area of skin is assessed with cross-polarized light the area is pretreated with a lotion. The area could then be compared to areas of skin that were irritated, but which did not receive any lotion. Further, an area of skin may be irritated, and then assessed using cross-polarized light after which the area is post-treated with a lotion. The area of skin could then be assessed again using cross-polarized light to determine if the lotion had an effect on the irritation.

Lotion may be in the form of emulsions or dispersions, and contain solids, gel structures, polymeric material, a multiplicity of phases (such as oily and water phase) and/or emulsified components. The lotion may be shear thinning, or may strongly change viscosity around skin temperature to allow for transfer and easy spreading on a user's skin. The lotion may sooth, moisturize, or lubricate a user's skin.

EXAMPLES OF THE PRESENT INVENTION

Test participants (participants) for the tests vary in age between eighteen (18) and sixty-five (65), and have very sensitive to moderately sensitive skin (Types I-IV) as determined by the previously mentioned Fitzpatrick's classifications. Test sites on three areas of skin are tested, namely the upper arm, forearm, and the skin area behind the knee (popliteal fossa). A test comprises application of test materials (patches/pads) to test sites on an area of skin, wherein the test sites are scored for erythema.

Each participant has two (2) to three (3) test sites identified for both the upper arm and forearm areas of each arm. Each test site is then demarcated on the lateral surface of the upper arm between the shoulder and elbow and the volar surface of the forearm. Such demarcation can be done in manners known to one of ordinary skill in the art, such as marking the test sites with 0.5% Gentian violet to ensure that patches are applied to the same test sites each day for the duration of a test. Test sites are measured four (4) cm×four (4) cm, and with a minimum of two (2) cm between test sites. Patches applied at the test sites are occluded patches containing 0.3 ml of saline or saline/SLS with differing concentrations of SLS (0.01%, 0.025%, 0.05%, 0.1%). All patches are a Webril® patch covered by an occlusive, hypoallergenic Blenderm® tape. Patches are removed by the participants thirty (30) to sixty (60) minutes prior to returning to the laboratory for scoring and/or reapplication of patches.

Test sites for the popliteal fossa are identified and then demarcated as stated above for the upper arm and forearm test sites. Test material for the popliteal fossa test sites is a currently-marketed brand of feminine hygiene pads. The pad is an ALWAYS® Feminine Sanitary Napkin. The pad is placed horizontally on the popliteal fossa, and held in place by an elastic knee band such as either Ace® Brand Knee Braces, Franklin Lakes, N.J., or Mueller Sport Care Elastic Knee Braces, Prairie du Sac, Wis. Pads are removed by the participants thirty (30) to sixty (60) minutes prior to returning to the laboratory for scoring and/or reapplication of materials.

In all tests, visual scoring of erythema at a test site is conducted by expert scorers under a 100 watt incandescent daylight bulb. Subsurface scoring of erythema at a test site was also conducted by expert scorers using the Syris v600™ polarized light visualization system recording a score for cross-polarizing illumination (subsurface visualization). Scoring of the test sites is done at the time points of baseline (prior to the first patch/pad application), post patch (thirty (30) to sixty (60) minutes after removal of each patch/pad), and recovery (twenty-four (24) hours after patch/pad application)). The detection and assessment (scoring) of erythema was used in the tests as an indicator of skin irritation.

Skin erythema was scored using a scale "0" to "4" as set out below in Table 1.

TABLE 1

Erythema Scoring Scale

| | |
|---|---|
| 0 | No apparent cutaneous involvement |
| 0.5 | Faint, barely perceptible erythema |
| 1 | Faint, but definite erythema |
| 1.5 | Well-defined erythema |
| 2 | Moderate erythema; may have papules or deep fissures |
| 2.5 | Moderate erythema with barely perceptible edema; may have a few papules |
| 3 | Severe erythema (beet redness); may have generalized papules |
| 3.5 | Moderate-to-severe erythema with moderate edema |
| 4 | Moderate-to-severe erythema and/or extending edema, may have generalized vesicles or eschar formations |

Erythema was scored according to Table 1, where "0" is no apparent cutaneous involvement and "4" is moderate-to-severe spreading erythema and/or edema. If after scoring a test site exhibits an erythema score of "2" or higher, that test site receives no further treatment in the form of applied patches/pads. However, the test site is still scored until completion of the test. Any test site showing an erythema score of "2" or more at the final scoring time point was followed until the erythema score regressed to a "1.5" or less. For each patch/pad, the average for all erythema scores among the test sites on an area of skin is calculated for each completed grading day, and reported as the mean erythema score for that area of skin on that particular grading day.

The same scorer was used throughout a test, and the scorer was not aware of which patch/pad had been applied to a test site. Additionally, for the duration of a test a new patch/pad applied to a test site was the same as the patch/pad that was removed from the test site. For example, if a patch containing 0.1% SLS would be replaced with another patch containing 0.1% SLS.

Example 1

24 Hour Upper Arm Patch Tests

Figure 1B:
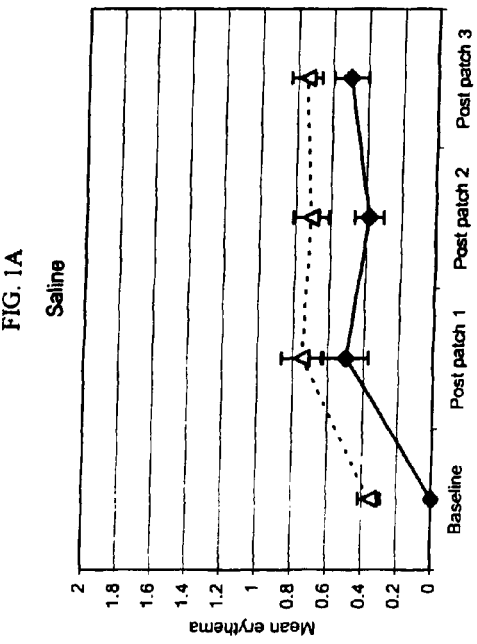
FIG. 1B is a graph illustrating the visual and subsurface mean erythema scores of upper arm test sites to which a patch containing 0.025% SLS has been applied.
Figure 1C:
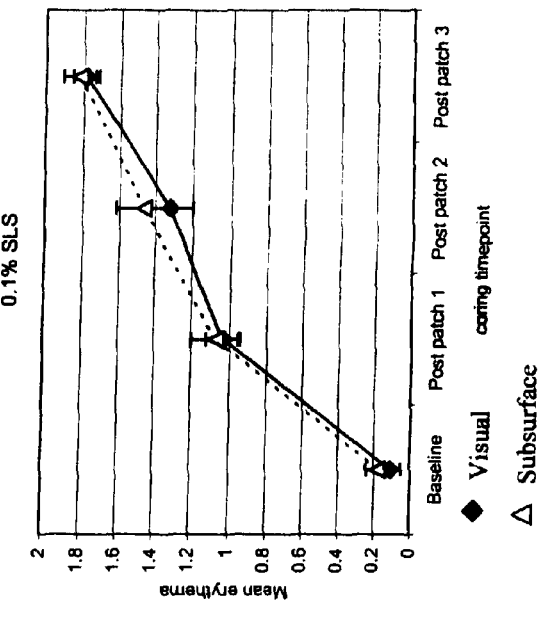
FIG. 1C is a graph illustrating the visual and subsurface mean erythema scores of upper arm test sites to which a patch containing 0.05% SLS has been applied.
Figure 1D:
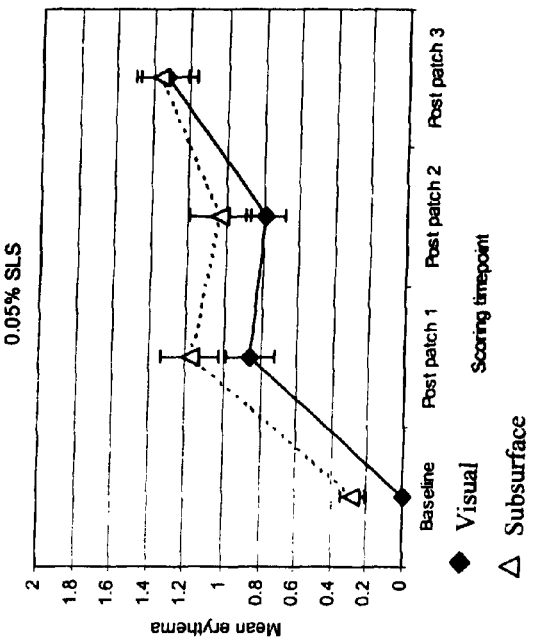
FIG. 1D is a graph illustrating the visual and subsurface mean erythema scores of upper arm test sites to which a patch containing 0.1% SLS has been applied.

Patches in the twenty-four (24) hour test comprised saline, FIG. 1A, and mixtures of saline and differing SLS concentrations (0.025%—FIG. 1B, 0.05%—FIG. 1C, 0.1%—FIG. 1D). Fourteen (14) participants were patched on their upper arms for three (3) days with a saline and/or saline/SLS containing patch. Before the patches were applied, a baseline mean erythema score using visual assessment and cross-polarized light was taken of each test site to which a patch was applied. About twenty-four (24) hours after application, the patch was removed and the test site scored (post patch 1), using visual assessment and cross-polarized light. A new patch was then applied to the test site and the procedure repeated twice more to produce two additional scores at post patch time points 2 and 3. In the twenty-four (24) hour patch test, the pattern of mean erythema scores using cross-polarized light was similar to the mean erythema scores resulting from the visual assessment. In the tests shown in FIGS. 1A-D, the mean erythema score using cross-polarized light and visual assessment after the first twenty-four (24) hour patch application to the upper arm was significantly different from the baseline mean erythema score. For all test concentrations of SLS (0, 0.025%, 0.05% and 0.1%), both the visual and cross-polarized light erythema score remained significantly elevated over baseline with subsequent patch applications (post patch 2 and 3). Illustrating that the use of cross-polarized light could track increases in subsurface erythema.

Example 2

6 Hour Upper Arm/Forearm Patch Tests

Figure 2A:
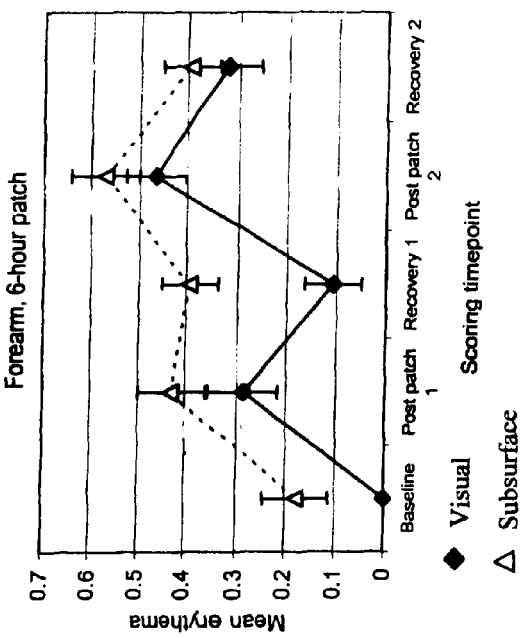
FIG. 2A is a graph illustrating the visual and subsurface mean erythema scores of forearm test sites to which a patch containing 0.01% SLS has been applied for two (2) hours.
Figure 2B:
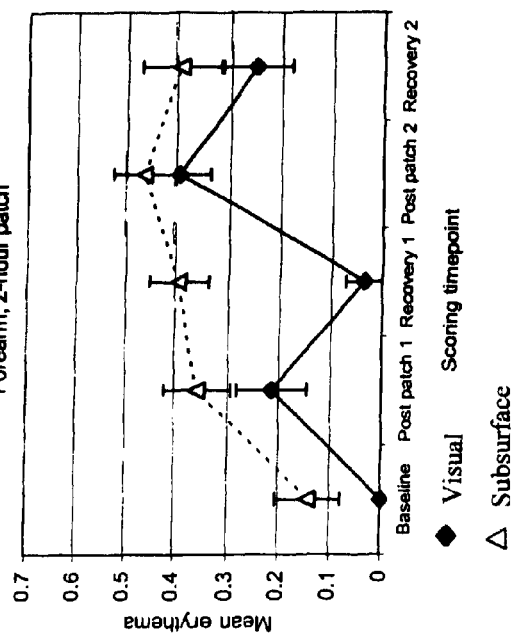
FIG. 2B is a graph illustrating the visual and subsurface mean erythema scores of forearm test sites to which a patch containing 0.01% SLS has been applied for six (6) hours.
Figure 2C:
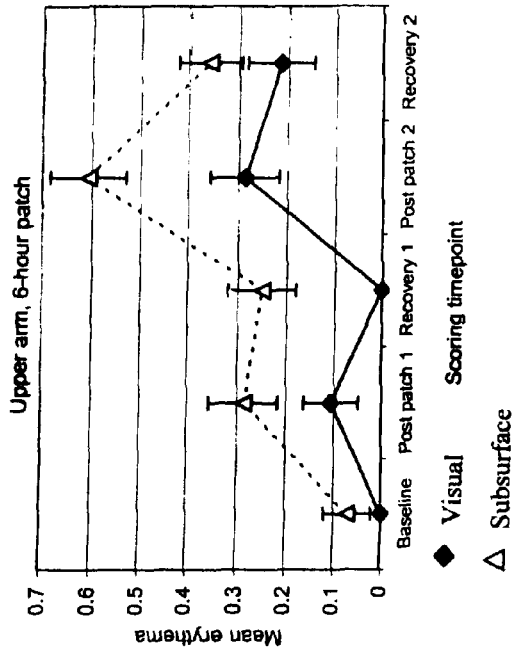
FIG. 2C is a graph illustrating the visual and subsurface mean erythema scores of upper arm test sites to which a patch containing 0.01% SLS has been applied for two (2) hours.
Figure 2D:
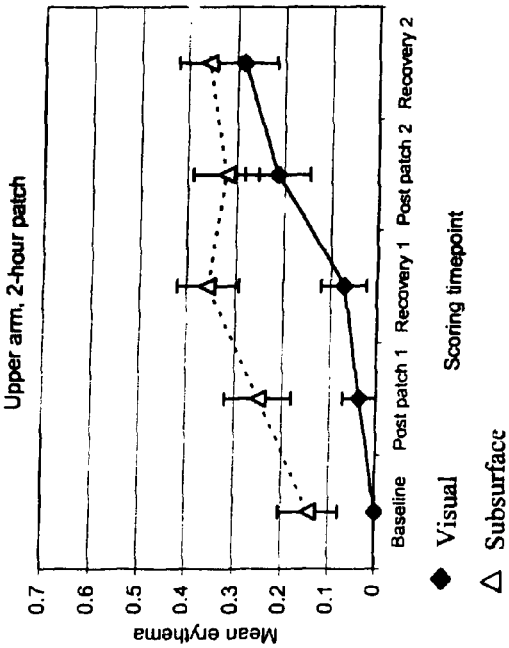
FIG. 2D is a graph illustrating the visual and subsurface mean erythema scores of upper arm test sites to which a patch containing 0.01% SLS has been applied for six (6) hours.

For two (2) days patch tests were conducted on the upper arms and forearms of fourteen (14) participants using patches containing SLS at a concentration of 0.01%. A baseline mean erythema score was taken as described in Example 1. Patches were then applied to the test sites for about two (2) hours to the forearms (FIG. 2A) and upper arms (FIG. 2C) of fourteen (14) participants, then removed and the test site scored (post patch time point 1), using visual assessment and cross-polarized light. About twenty-four (24) hours after the application of the first patch the test site was scored again (recovery time point 1), as for post patch time point 1. A second patch was applied to the same test site and after about two (2) hours the patch was removed and the test site scored (post patch time point 2) as before. About twenty-four (24) hours after the application of the second patch the test site was scored again as done previously (recovery time point 2). The same procedure was done for the forearm (FIG. 2B) and upper arm (FIG. 2D) (two six hour applications of a patch with about twenty-four (24) hours between patch applications), but applying a patch for about six (6) hours to a test site instead of about two (2) hours. On the forearm, scoring with cross-polarized light detected significant increases in the mean erythema score compared to baseline after a single patch application (post patch time point 1) for about two (2) hours (FIG. 2A) and about six (6) hours (FIG. 2B). On the upper arm, scoring with cross-polarized light detected significant increases in the mean erythema score after a single application (post patch time point 1) for about six (6) hours (FIG. 2D). With a patch exposure of about two (2) hours (FIG. 2C) on the upper arm, the increase in subsurface erythema was not noticeable immediately after patch removal, but was significant after about twenty-four (24) hours of recovery (recovery time point 1).

In all tests (FIGS. 2A-2D) the mean erythema scores resulting from the use of cross-polarized light were higher at all time points than the mean erythema scores resulting from visual assessment. Visual assessment on the forearm for both the two (2) hour test (FIG. 2A) and six (6) hour test (FIG. 2B) resulted in a mean erythema score that was significantly elevated immediately after removal of the first patch (post patch time point 1), but which dropped to near baseline levels after the first recovery time point (recovery time point 1). In comparison, the mean erythema scores resulting from the use of cross-polarized light at the first recovery time point (recovery time point 1) were not noticeably reduced in the case of the six (6) hour test (0.42 to 0.4) and in the two (2) hour test the mean erythema score increased (0.35 to 4.0). Both tests for the upper arm (FIGS. 2C and 2D) also show that at the first recovery time point (recovery time point 1) the mean erythema scores resulting from the use of cross-polarized light (FIG. 2C—0.35, FIG. 2D—0.25) are significantly higher than the mean erythema scores from the visual assessment (FIG. 2C—0.8, FIG. 2D—0).

Example 3

Popliteal Fossa Tests

Figure 3A:
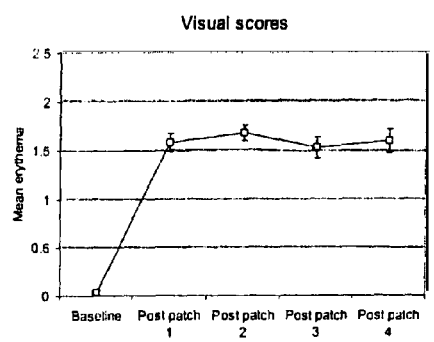
FIG. 3A is a graph illustrating the visual post patch mean erythema scores of popliteal fossa test sites to which a pad has been applied.
Figure 3B:
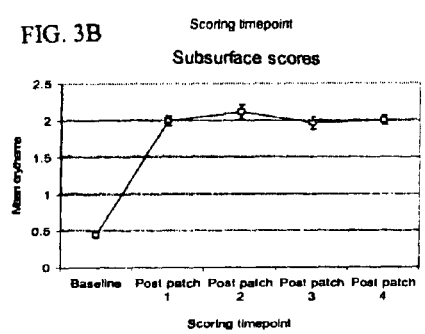
FIG. 3B is a graph illustrating the subsurface post patch mean erythema scores of popliteal fossa test sites to which a pad has been applied.
Figure 3C:
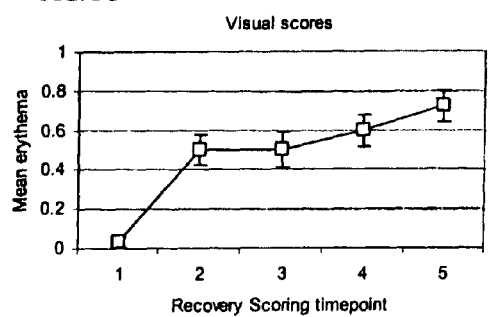
FIG. 3C is a graph illustrating the visual recovery mean erythema scores of popliteal fossa test sites to which a pad has been applied.
Figure 3D:
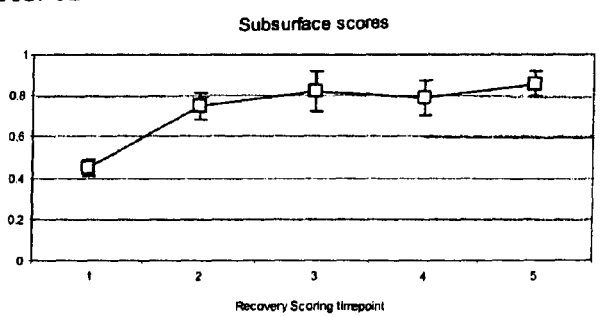
FIG. 3D is a graph illustrating the subsurface recovery mean erythema scores of popliteal fossa test sites to which a pad has been applied.

A baseline mean erythema score, as described in Example 1, was taken for each test site located at the popliteal fossa of the fourteen (14) participants to which a pad was applied. Pads were then applied to the test sites for about six (6) hours per day for four (4) consecutive days. A first pad was applied to a test site for about six (6) hours then removed, and the test site scored (post patch time point 1), using visual assessment and cross-polarized light. About twenty-four (24) hours after the first pad was applied to a test site, the test site was scored again (recovery time point 1), as before and a second pad applied for about six (6) hours. This procedure was repeated three (3) more times to produce mean erythema scores at post patch time points 2-4 and recovery time points 2-4. As shown in FIGS. 3A and 3B, the first scoring conducted immediately after removal of the first test sample at post patch time point 1 was significantly higher than the baseline mean erythema score. Additionally, the mean erythema scores using cross-polarized light were significantly higher for the pad (FIG. 3B and FIG. 3D) at all recovery time points and post patch time points, as compared to the visual mean erythema scores (FIG. 3A and FIG. 3C).

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

All documents cited in the Detailed Description of the Invention are, in relevant part, incorporated herein by reference; the citation of any document is not to be construed as an admission that it is prior art with respect to the present invention. To the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A method of assessing mucosal tissue irritation comprising:
    a. providing a personal care article;
    b. contacting the personal care article with an area of mucosal tissue;
    c. providing an instrument that uses a polarized illuminating light, combined with polarized viewing;
    d. illuminating the area of mucosal tissue with the cross-polarized light; and
    e. using the instrument to view below the surface of the mucosal tissue to determine a level of erythema present below the mucosal tissue surface;
    f. assigning a score to the level of erythema determined in step e;
    g. using the score to assess the presence of mucosal tissue irritation.

2. The method of claim 1 wherein the personal care article comprises at least one of a feminine care product, adult incontinence product, sanitary tissue product, baby care product, home care product, beauty care product, or oral care product.

3. The method of claim 1 wherein the personal care article irritates the area of mucosal tissue.

4. The method of 3 wherein the personal care article irritates the area of mucosal tissue by at least one of chemical means or physical means.

5. The method of claim 1 wherein the area of mucosal tissue is treated with a lotion.

6. The method of claim 5 wherein the area of mucosal tissue is treated with the lotion before contacting the personal care article with the area of mucosal tissue.

7. The method of claim 5 wherein the area of mucosal tissue is treated with the lotion after contacting the personal care article with the area of mucosal tissue, but before using the instrument to view below the surface of the mucosal tissue to determine the level of erythema present below the mucosal tissue surface.

* * * * *